United States Patent
Be'eri et al.

(10) Patent No.: US 7,096,866 B2
(45) Date of Patent: Aug. 29, 2006

(54) INEXSUFFLATOR

(75) Inventors: Eliezer Be'eri, Jerusalem (IL); Eliyahu Raphael Malka, Ramat Gan (IL); Yisrael Shuchman, Jerusalem (IL)

(73) Assignee: Alyn Woldenberg Family Hospital, Jerusalem (IL)

( * ) Notice: Subject to any disclaimer, the term of this patent is extended or adjusted under 35 U.S.C. 154(b) by 315 days.

(21) Appl. No.: 10/211,544

(22) Filed: Aug. 5, 2002

(65) Prior Publication Data

US 2003/0051729 A1 Mar. 20, 2003

Related U.S. Application Data

(63) Continuation-in-part of application No. 09/975,943, filed on Oct. 15, 2001, now abandoned.

(30) Foreign Application Priority Data

Sep. 16, 2001 (IL) .................................. 145461

(51) Int. Cl.
*A62B 16/08* (2006.01)

(52) U.S. Cl. ..................... 128/205.19; 128/205.24; 128/205.25

(58) Field of Classification Search ........... 128/205.13, 128/205.14, 205.17, 205.19; 482/13
See application file for complete search history.

(56) References Cited

U.S. PATENT DOCUMENTS

| | | | | |
|---|---|---|---|---|
| 1,343,486 A | * | 6/1920 | Stolle | 128/204.25 |
| 1,358,893 A | * | 11/1920 | Stolle | 128/204.25 |
| 2,535,844 A | * | 12/1950 | Emerson | 128/200.21 |
| 2,914,064 A | * | 11/1959 | Sandelowsky | 128/205.19 |
| 4,193,406 A | * | 3/1980 | Jinotti | 128/204.18 |
| 4,320,754 A | * | 3/1982 | Watson et al. | 128/204.25 |
| 4,456,008 A | * | 6/1984 | Clawson et al. | 128/205.19 |
| 4,705,073 A | * | 11/1987 | Beck | 137/625.25 |
| 5,191,881 A | * | 3/1993 | Beck | 128/205.24 |
| 5,211,171 A | * | 5/1993 | Choromokos | 128/205.19 |
| 5,309,904 A | * | 5/1994 | Beck | 128/205.24 |
| 5,313,938 A | * | 5/1994 | Garfield et al. | 128/205.16 |
| 5,345,930 A | * | 9/1994 | Cardinal et al. | 128/205.24 |
| 6,062,217 A | * | 5/2000 | Gray | 128/205.13 |
| 6,427,691 B1 | * | 8/2002 | Jinotti | 128/205.24 |

FOREIGN PATENT DOCUMENTS

| | | |
|---|---|---|
| DE | 1255865 | 12/1967 |
| GB | 1208775 | 10/1970 |

OTHER PUBLICATIONS

Bach, M.D., John R., "Noninvasive Mechanical Ventilation," *Hanley & Belfus, Inc.*, publishers, Chpt. 7, pp. 151-163.
J.H. Emerson Co., "cough assist: User's Guide," CoughAssist User's Guide Supplement—910-1200-0, Modes CA-3000, CA-3200, CM-3000 and CM-3200.

* cited by examiner

*Primary Examiner*—Gary Jackson
*Assistant Examiner*—Michael Mendoza
(74) *Attorney, Agent, or Firm*—Lahive & Cockfield, LLP

(57) ABSTRACT

A manual inexsufflator including a standard mechanical ventilator, a medical suction unit, and a piston-like sliding valve mechanism which connects a patient ventilation interface with either the ventilator or the suction unit. By sliding the valve mechanism in and out the user selectively connects the patient to either the ventilator, for purposes of insufflation, or the suction unit, for purposes of exsufflation. The ventilator may generate expiratory positive airway pressure between inexsufflation cycles.

6 Claims, 2 Drawing Sheets

INEXSUFFLATOR

CROSS-REFERENCE TO PREVIOUS APPLICATIONS

This application is a continuation-in-part application of and claims priority from U.S. patent Ser. No. 09/975,943, filed Oct. 15, 2001, now abandoned.

FIELD OF THE INVENTION

The present invention relates generally to respiratory apparatus, and particularly to an inexsufflator useful, for example, in clearing respiratory secretions from airways.

BACKGROUND OF THE INVENTION

Patients suffering from weakness of the muscles of the thoracic cage and diaphragm, as may occur in, for example, Duchenne Muscular Dystrophy or Cervical Spine Injury, are often unable to cough effectively, if at all. Due to their inability to clear respiratory secretions from their lower respiratory tract, retained secretions may develop in their lungs. As retained secretions constitute a focus for infection, these patients are at high risk of developing severe, and potentially fatal, pneumonia, and are thus in need of assistance in expectorating their respiratory secretions.

Several techniques for assisting such patients are known. If the degree of muscle weakness is mild, physical therapy techniques such as "manually assisted coughing" may be effective. With this technique, the therapist enhances the efficacy of the patient's natural cough by means of a hand thrust on the patient's ribcage or abdomen, timed in coordination with the patient's natural coughing action. If the degree of muscle weakness is severe, however, the patient will require mechanical assistance to achieve adequate pulmonary toilet.

For patients who are intubated with an endotracheal tube, or have a permanent tracheostomy cannula in place (either of which may be necessary for purposes of mechanical ventilation due to the severity of the chest wall muscle weakness), endotracheal suction is commonly used as a technique for secretion clearance. Endotracheal suction is achieved by inserting a narrow gauge catheter into the patient's trachea via a larger gauge endotracheal tube or tracheostomy cannula, and then applying suction through the catheter. Secretions that are in proximity to the tip of the catheter are then sucked into the catheter and removed. This technique achieves secretion removal by utilizing a suction force to cause secretions to either adhere to the catheter tip or enter into the catheter, which is then withdrawn from the body while the suction force is maintained. It should be noted that the suction is generated within the suction catheter only, not within the endotracheal tube or tracheostomy cannula, and that it is executed at any stage during the patient's respiratory cycle, be it inspiration or expiration.

There are several drawbacks to endotracheal suction as a means for clearing respiratory secretions. The procedure is invasive, thus requiring sterile technique for its performance, and may cause physical trauma to, or infection within, the patient's airways. Moreover, this technique can only be performed on those patients who are already intubated or tracheostomized, and is not relevant to the majority of patients who do not have instrumentation within their respiratory tract.

For non-intubated patients, and for intubated patients who wish to avoid the above-mentioned drawbacks of endotracheal suction, a desirable mechanical method for removal of tracheobronchial secretions is that of mechanical insufflation-exsufflation (also known as inexsufflation), by means of an inexsufflator. The Concise Oxford Dictionary, Seventh Edition, Oxford University Press, 1985, defines insufflation as "blowing air into a cavity of the body", and Blackiston's Gould Medical Dictionary, Fourth Edition, McGraw-Hill, 1979, defines exsufflation as "forcible expiration; forcible expulsion of air from lungs by a mechanical apparatus".

Most commonly, an inexsufflator is applied to a patient's respiratory tract via a facemask held hermetically over the patient's mouth and nose, a nasal mask, nasal prongs, or a mouthpiece held in the patient's mouth. All of the aforementioned are hereinafter referred to as "noninvasive ventilation interfaces", by which is meant a ventilation interface that does not penetrate into the patient's trachea, but rather interfaces with the patient's mouth and/or nose. Alternatively, if the patient is intubated or has a tracheostomy, the inexsufflator may be attached directly to the endotracheal tube or tracheostomy cannula (which are "invasive ventilation interfaces"). Typically, an inexsufflator functions in a cyclical fashion as follows: First, the inexsufflator mechanically pumps air into the patient's lungs until the lungs have expanded to their maximum capacity (insufflation). Then, at the moment of peak insufflation, the inexsufflator rapidly sucks air out of the patient's lungs at a high flow rate. This rapid flow of air through the patient's respiratory tract outward (exsufflation) carries with it secretions from the lower respiratory tract. In this manner, an inexsufflator artificially simulates the action of a natural cough.

Thus, in contrast to endotracheal suction, inexsufflation is noninvasive (and thus does not require sterile technique or cause trauma to the airways), and achieves secretion removal by causing rapid airflow (at least 160 liters/minute) through the entire respiratory tree, as occurs during a physiological cough. This airflow "blows" the secretions up the trachea and into the patient's mouth (or tracheostomy cannula/endotracheal tube if the patient is intubated).

Many patients in need of an inexsufflator have weakness of their facial and glossopharyngeal muscles in addition to the weakness of their chest wall muscles, and they typically are unable to "hold in" a deep breath for a significant period of time. As such, after an inexsufflator completes the lung insufflation cycle, the insufflated air may rapidly dissipate through the patient's mouth and nose. It is thus of critical importance for the successful functioning of an inexsufflator that the cycle of mechanical exsufflation commences immediately after full insufflation has been achieved, prior to air dissipation, because if the onset of exsufflation is even marginally delayed the volume of air within the patient's lungs which will be available for mechanical exsufflation will be significantly diminished, resulting in an ineffective "cough".

Mechanical inexsufflation is particularly effective when it is augmented by the manual assisted cough technique described above. This is usually done by a single caregiver (often a physiotherapist or a member of the patient's family) who operates the inexsufflator while simultaneously applying abdominal/chest thrusts timed to the exsufflation phase of the machine.

It is physiologically desirable that each insufflation-exsufflation cycle be separated from the preceding or following cycle by a pause of at least a few seconds, so as to prevent hyperventilation of the patient. During this expiratory pause period no airflow is generated by the inexsufflator, such that the intrapulmonary pressure equilibrates to atmospheric pressure (that is, zero) during this time, until the onset of the next insufflation.

Standard inexsufflators, such as the CoughAssist Inexsufflator (J. H. Emerson Co. Cambridge, Mass.) utilize a blower to generate airflow within the machine. This mechanism is used to generate airflow alternately in two directions: into the lungs under positive pressure during insufflation, and out of the lungs under negative pressure during exsufflation. In the "automatic" version of this machine, model CA-3000, cycling from insufflation to exsufflation is achieved by means of an electrically operated switching mechanism that automatically redirects the direction of airflow between the patient and the machine (either into or out of the blower) according to a predefined time sequence. Alternatively, the operator can control the timing of the insufflation-exsufflation cycles by pushing an electric switch in a respectively rightward or leftward direction while the machine is operating, in accordance with the time sequence desired by the operator.

The electrical timing mechanism within automatic inexsufflators, and the mechanism for generating positive-pressure airflow into the patient, makes these devices both electronically complex and expensive. The cost of such devices (approximately $5000 in 2002) is of particular importance because many patients in need of an inexsufflator are concurrently in need of a similarly expensive mechanical ventilator for purposes of mechanical ventilation via an invasive or noninvasive ventilation interface, as their chest wall muscle weakness limits not only their ability to cough, but also their ability to breath adequately and independently. Such patients, who are often already using a mechanical ventilator, are thus compelled to acquire an additional expensive ventilatory device if they wish to perform mechanical inexsufflation.

So as to decrease the cost of standard inexsufflator devices, "manual" versions of the CoughAssist Inexsufflator have been developed, such as the CoughAssist model CM-3000 (J. H. Emerson Co. Cambridge, Mass.), which does not have an electrical timing mechanism. In this manual version, the operator manually controls the timing of the insufflation-exsufflation cycles by swiveling or rotating a mechanical non-electronic handle to-and-fro in a respectively rightward or leftward direction, so as to mechanically redirect the direction of patient airflow into or out of the blower.

Standard inexsufflators, however, are known to suffer from several deficiencies:

1) The equilibration of intrapulmonary pressure with atmospheric pressure that occurs during the expiratory pause phase of the respiratory cycle impedes effective secretion clearance. This is because the lack of positive (i.e. supra-atmospheric) intrapulmonary pressure during this period encourages the collapse of smaller airways and alveoli, which traps secretions deep within the lung.

2) Standard inexsufflators are comprised of a built-in mechanism for generating airflow in two directions (both into and out-of the patient's lungs), which is mechanically complex. As such, standard inexsufflators (both manual and automatic versions) are expensive, with even manual inexsufflators costing approximately $3000 in 2002.

3) It is difficult for a caregiver performing the manual assisted cough technique simultaneously with mechanical inexsufflation to achieve optimal coordination with a manual inexsufflator. This is because each of the caregiver's hands have to perform a different maneuver simultaneously: while one hand has to perform an "in-out" abdominal/chest thrust on the patient, the other hand has to perform a "side-to-side" rotary movement of the swivel handle on the manual inexsufflator. Precise coordination of left and right hand movements, which is essential for achievement of effective cough flows, is particularly difficult when each hand is performing a different gross motor movement.

SUMMARY OF THE INVENTION

The present invention seeks to provide a manual inexsufflator that is simple and inexpensive, yet efficient and effective in artificially reproducing a coughing action to clear respiratory secretions from lungs and airways.

In general terms, the inexsufflator of the current invention may comprise three primary components: 1) a mechanical ventilator, 2) a suction unit, and 3) a sliding, piston-like, valve mechanism, which connects the above two components to a patient ventilation interface (such as a noninvasive or an invasive ventilation interface).

Each of the three primary components may be easily attached to and detached from each other by means of standard ventilator tubing. Any type of standard mechanical ventilator, including ventilators of the type used by patients with chest wall weakness for purposes of mechanical ventilation, may be used as part of the inexsufflator of the current invention. The same ventilator may concomitantly be used by the patient for regular mechanical ventilation between inexsufflation sessions. Consequently, for the many patients who already possess standard ventilators, only the piston-valve and suction components of the current invention need be added so as to "convert" their ventilators into inexsufflators, in terms of the current invention. As such, for a patient who already owns a ventilator, acquiring the current invention entails substantially less expense than that entailed in acquiring an independent, standard inexsufflator.

In one embodiment of the current invention, the mechanical ventilator is of a type that is capable of actively generating and maintaining positive end-expiratory pressure (PEEP), also known as expiratory positive airway pressure, during the pause between inexsufflation cycles.

The piston-valve establishes airflow continuity between the patient interface and, depending on the valve's orientation (i.e., piston "pushed in" or piston "pulled out"), either the ventilator or the suction unit, both of which operate continuously. The operator of the inexsufflator causes the device to cycle between insufflation and exsufflation by manually pulling the piston of the valve outward (when the ventilator is delivering a breath) and then pushing it inward (at the moment that mechanical inhalation terminates). In so doing, the operator selectively and exclusively establishes airflow continuity between the patient and either the mechanical ventilator (thus achieving insufflation) or the suction unit (thus achieving exsufflation) in an alternating manner respectively. Between inexsufflation cycles the piston is pulled outwards, so that the ventilator delivers PEEP to the patient until the onset of the next mechanical breath. As such, intra-alveolar pressure does not remain at zero after exsufflation has terminated, thus preventing alveolar or airway collapse The "in-out" movement of the piston-valve parallels the arm action of an abdominal/chest thrust as is done for purposes of assisted coughing. Thus, an operator performing an abdominal thrust with one hand while initiating a mechanical exsufflation with the other hand performs the same gross motor movement with each hand simultaneously.

This uniformity of hand movement facilitates exact coordination of the two actions by the operator, thus enhancing the efficacy of the procedure.

In an embodiment of the invention, an external mechanical ventilator may be used for generating insufflation in the current invention, rather than a dedicated, "built-in" source of positive pressure airflow. An expiratory positive airway pressure may be generated during the pause between insufflation-exsufflation cycles, by means of the mechanical ventilator.

The manual valve mechanism may be operated by an "in-out" or "push-pull" type of hand/arm movement, rather than a "side-to-side" rotary movement.

There is thus provided in accordance with a preferred embodiment of the present invention an inexsufflator including a patient interface unit, a source of negative fluid pressure, a source of positive fluid pressure, wherein the source of positive fluid pressure includes at least one of a mechanical ventilator operative to generate an expiratory positive airway pressure and a volume-cycled mechanical ventilator, and a valve connected to the source of positive fluid pressure and the source of negative fluid pressure, the valve being adapted to selectively connect the patient interface unit with the source of positive fluid pressure and the source of negative fluid pressure.

Further in accordance with a preferred embodiment of the present invention the valve includes a manual valve.

In accordance with a preferred embodiment of the present invention the manual valve includes a sliding element.

There is also provided in accordance with a preferred embodiment of the present invention an inexsufflator including a patient interface unit, a source of negative fluid pressure, a source of positive fluid pressure, and a manual valve connected to the source of positive fluid pressure and the source of negative fluid pressure, the valve being adapted to selectively connect the patient interface unit with the source of positive fluid pressure and the source of negative fluid pressure, and the valve including a sliding element.

In accordance with a preferred embodiment of the present invention the patient interface unit includes a noninvasive ventilation interface.

In accordance with a preferred embodiment of the present invention the manual valve is adapted to substantially seal fluid flow from the source of positive fluid pressure to the patient interface unit while generally simultaneously opening fluid flow from the source of negative fluid pressure to the patient interface unit.

Further in accordance with a preferred embodiment of the present invention the inexsufflator includes a working cycle that includes providing positive fluid pressure from the source of positive fluid pressure via the valve to the patient interface unit, and, within a predetermined period of time, substantially sealing fluid flow from the source of positive fluid pressure to the patient interface unit while generally simultaneously providing negative fluid pressure from the source of negative fluid pressure via the valve to the patient interface unit.

Still further in accordance with a preferred embodiment of the present invention at least one pressure sensor is adapted to sense at least one of the positive fluid pressure and the negative fluid pressure.

Further in accordance with a preferred embodiment of the present invention the sliding element includes a first orientation and a second orientation, wherein in the first orientation the sliding element permits fluid flow from the source of positive fluid pressure to the patient interface unit, but substantially seals fluid flow from the source of negative fluid pressure to the patient interface unit, and in the second orientation the sliding element substantially seals fluid flow from the source of positive fluid pressure to the patient interface unit but permits fluid flow from the source of negative fluid pressure to the patient interface unit.

Still further in accordance with a preferred embodiment of the present invention the sliding element includes a piston that slides in a housing between the first and second orientations.

In accordance with a preferred embodiment of the present invention the piston has an aperture formed therein adapted to be selectively in fluid communication with an opening formed in the housing.

Further in accordance with a preferred embodiment of the present invention the sliding element includes a sealing element that is in selectively sealed engagement with the piston.

Further in accordance with a preferred embodiment of the present invention the source of negative fluid pressure includes a medical suction unit.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
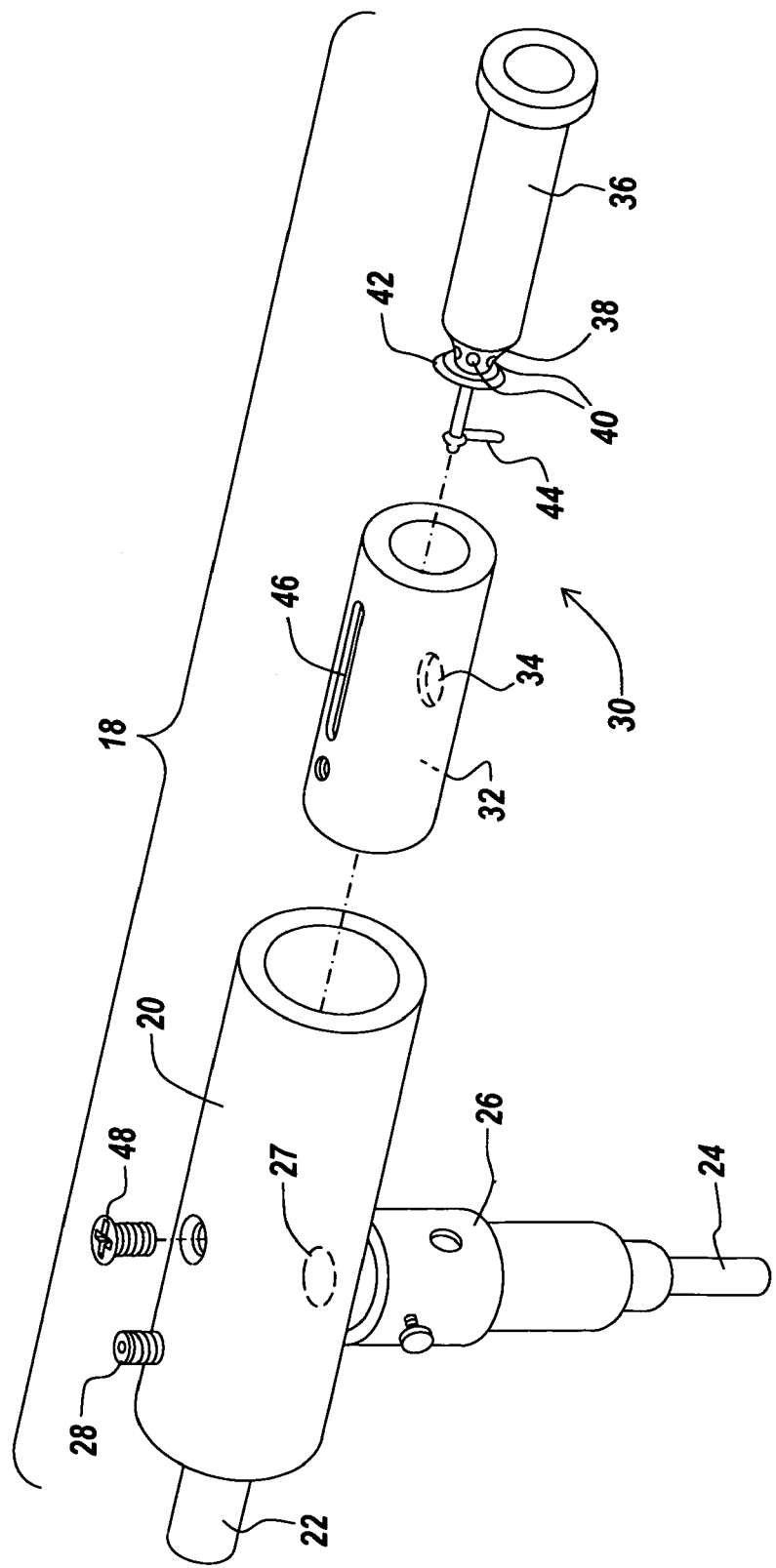
FIG. 1 is a simplified pictorial, exploded illustration of an inexsufflator constructed and operative in accordance with a preferred embodiment of the present invention.
Figure 2:
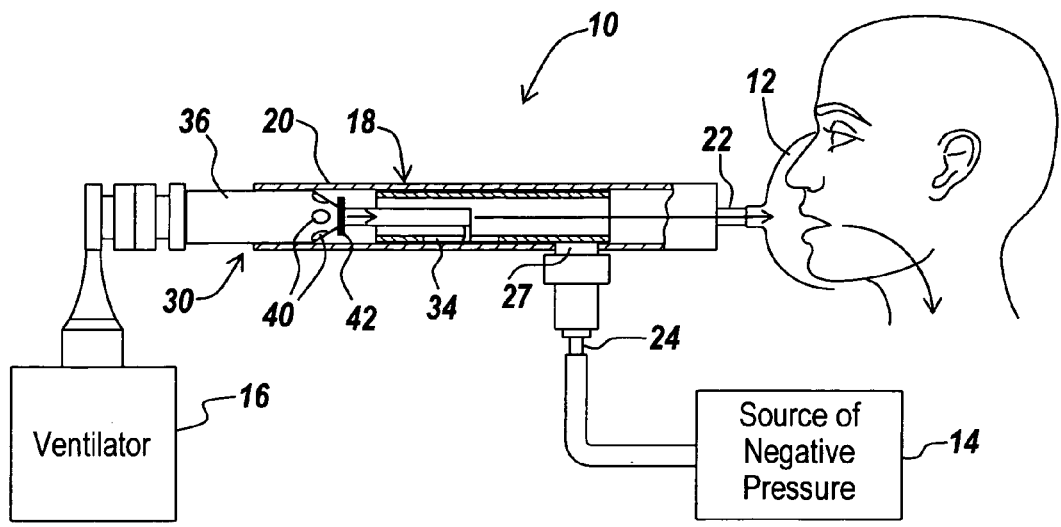
FIG. 2 is a simplified pictorial illustration of the inexsufflator of FIG. 1 in a first orientation comprising insufflation of a patient, in accordance with a preferred embodiment of the present invention.

Reference is now made to FIGS. 1 and 2, which illustrate an inexsufflator 10 constructed and operative in accordance with a preferred embodiment of the present invention.

Inexsufflator 10 preferably includes a patient interface unit 12 (FIG. 2), which may comprise, without limitation, an invasive ventilation interface (for example, a tube connector that connects directly to a tracheostomy cannula, not shown) or a noninvasive ventilation interface (for example, a facemask applied to a patient's face). A source 14 of negative fluid pressure may be provided, such as but not limited to, a standard medical suction unit, for example, an Accuvac Basic Aspirator (Gottlieb Weinmann GmbH & Co. Hamburg, Germany) a vacuum cleaner or any other suitable suction device. A source 16 of positive fluid pressure may be provided, such as but not limited to, a mechanical ventilator or an "AMBU" type manual resuscitator bag, for example. It is noted that the sources 14 and 16 of negative and positive fluid pressure, respectively, may be manually or automatically controllable with any suitable control apparatus, sensors, recording devices and the like (not shown).

A manual valve 18 is preferably connected to the source 14 of negative fluid pressure and to the source 16 of positive fluid pressure. Valve 18 is adapted to selectively connect patient interface unit 12 with sources 14 or 16 of negative and positive fluid pressure, respectively.

The following is one example of a construction of manual valve 18, although it is understood that the manual valve 18 is not limited to this construction. In the illustrated embodiment, manual valve 18 comprises a cylindrical housing 20 having a connector element 22 for connection to patient interface unit 12 and another connector element 24 for connection to the source 14 of negative fluid pressure. An aperture control device 26 may be provided at the interface between housing 20 and connector element 24 for varying the amount of negative pressure, i.e., controlling the amount of suction. Housing 20 may have an opening 27 that fluidly communicates with connector element 24. One or more pressure sensors 28 may be provided for sensing the positive fluid pressure or the negative fluid pressure, such as but not limited to, a Pitot tube or a manometer on housing 20 (pressure sensor 28 is omitted for clarity in FIGS. 2 and 3).

Manual valve 18 may comprise a sliding element 30 that may include a hollow cylindrical piston 32 that slides in housing 20. Piston 32 may have an aperture 34 formed therein adapted to be selectively in fluid communication with opening 27 of housing 20, as described more in detail hereinbelow. A sealing element 36 may be provided that is in selectively sealed engagement with piston 32 of sliding element 30. Sealing element 36 may comprise a hollow cylinder with a tapered end 38. Tapered end 38 may be formed with a plurality of openings 40 through which a fluid, such as air, may pass. A seal 42, such as an O-ring, may be placed at tapered end 38 proximal (i.e., closer to the connector element 22) to openings 40. Sealing element 36 may be coupled to piston 32, without limitation, by means of a tongue 44 that protrudes from a proximal end of sealing element 36 and which is received in aperture 34. A screw 48 may optionally protrude into a groove 46 on the outer surface of piston 32 and serve as a stop to limit the travel of piston 32 in housing 20.

Sliding element 30 comprises a first orientation and a second orientation. In the first orientation, shown in FIG. 2, sealing element 36 does not abut against piston 32 and fluid may flow from the source 16 of positive fluid pressure to patient interface unit 12. However, aperture 34 is not aligned with opening 27 of housing 20 and thus sliding element 30 substantially seals fluid flow from the source 14 of negative fluid pressure to patient interface unit 12.

Figure 3:
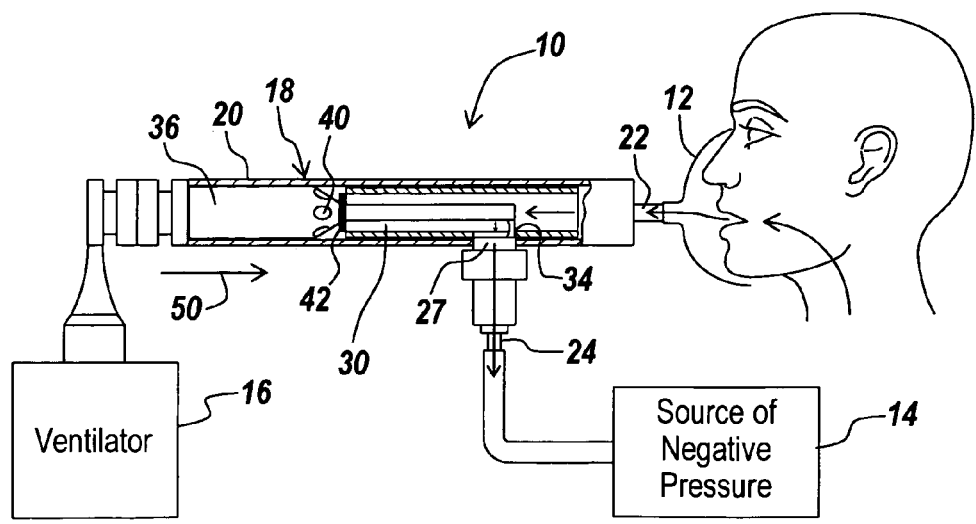
FIG. 3 is a simplified pictorial illustration of the inexsufflator of FIG. 1 in a second orientation comprising exsufflation of the patient, in accordance with a preferred embodiment of the present invention.

In the second orientation, shown in FIG. 3, sliding element 30 has been moved generally in the direction of an arrow 50 (towards the connector element 22 that connects to patient interface unit 12). In the second orientation, seal 42 of sealing element 36 abuts against piston 32 and substantially seals fluid flow from the source 16 of positive fluid pressure to patient interface unit 12. Tongue 44 is adapted to pull piston 32 when piston 32 is manually moved out of housing 20 by an operator of inexsufflator 10, and seal 42 is adapted to push piston 32 when piston 32 is moved into housing 20 by the operator of inexsufflator 10. Aperture 34 is now aligned with opening 27 of housing 20 and thus sliding element 30 permits fluid flow from the source 14 of negative fluid pressure to patient interface unit 12. Thus, manual valve 18 may operate like a two-way valve.

A working cycle of inexsufflator 10 for providing air to a patient and suddenly causing the patient to cough is now described with reference to FIGS. 2 and 3. In FIG. 2, source 16 of positive fluid pressure supplies positive fluid pressure via manual valve 18 to patient interface unit 12, which pressure is forced into the airways and respiratory system of the patient. The positive pressure may be monitored by observing pressure sensor 28. In particular, the user monitors pressure sensor 28 so as to discern the onset and peak of insufflation. At or near the moment of maximal lung insufflation, as depicted by an increase in the pressure recorded on pressure sensor 28 or as discerned by observation of the patient's chest wall movement, the user initiates exsufflation as follows: Within a predetermined period of time, preferably rapidly and suddenly so as to prevent air dissipation prior to the onset of exsufflation, the user moves manual valve 18 to the second orientation shown in FIG. 3. For example, the user may suddenly and quickly slide sliding element 30 in the direction of arrow 50, thereby substantially sealing fluid flow from the source 16 of positive fluid pressure to patient interface unit 12, while generally simultaneously providing negative fluid pressure from the source 14 of negative fluid pressure via manual valve 18 to patient interface unit 12. The sudden application of negative pressure to the lungs that have been insufflated with the positive pressure may generate a rapid airflow out of the lungs of the patient, thereby achieving exsufflation. During the process of exsufflation, the user monitors pressure sensor 28 so as to discern the degree of negative pressure being generated within the patient's airways. After a predetermined period of time, such as but not limited to about 1 second, or upon attainment of a desired degree of negative pressure within the airways, the manual valve may be returned to the first orientation so as to terminate the phase of exsufflation and start the working cycle again.

In a first embodiment of the current invention, source 16 of positive fluid pressure is a hand-held "AMBU" type manual resuscitator bag, for example, an MR-100 Adult Resuscitator (Galemed Corp. Taiwan). In terms of this embodiment, the phase of insufflation is initiated by the user manually squeezing the manual resuscitator bag so as to generate positive pressure within the patient's airways, as depicted by pressure sensor 28. Thereafter, the working cycle of inexsufflator 10 is generally as described previously. In terms of this embodiment of inexsufflator 10, intrapulmonary pressure returns to atmospheric pressure during the pause period between the termination of exsufflation and the initiation of the next insufflation.

In a second embodiment, source 16 of positive fluid pressure is a standard volume-cycled or time-cycled pressure-limited ventilator, for example, an LP-10 Volume Ventilator (Nellcor Puritan Bennet Inc. Pleasanton, Calif.) or an LTV-1000 Ventilator (Pulmonetic Systems, Colton, Calif.). A volume-cycled ventilator is a ventilator in which the amount of air delivered to the patient by the ventilator with each inspiration is a predefined volume of air. In other words, the ventilator terminates airflow and ends the phase of inspiration when a predefined volume of air has entered the patient. This is to be contrasted with a time-cycled ventilator, in which the amount of air delivered to the patient by the ventilator with each inspiration is of an a-priori undefined volume, and the ventilator terminates airflow and ends the phase of inspiration when a predefined inspiratory time has been achieved. Similarly, standard inexsufflators, such as the CoughAssist Inexsufflator, terminate positive pressure airflow and end the phase of insufflation when a predefined inspiratory time, but not volume, has been achieved.

In this second embodiment, prior to initiation of the working cycle described above, the user sets ventilation parameters for the ventilator so as to achieve maximal insufflation with each delivered ventilator breath, by choosing an appropriate value for the tidal volume (if a volume cycled ventilator is being used) or for the peak inspiratory pressure (if a time-cycled pressure-limited ventilator is being used). Thereafter, the working cycle of inexsufflator 10 is generally as described previously. As standard volume-cycled or time-cycled ventilators may not be capable of maintaining positive pressure within the patient's airway during expiration, in terms of this embodiment of inexsufflator 10 intrapulmonary pressure may return to atmospheric pressure during the pause period between the termination of exsufflation and the initiation of the next insufflation by the ventilator.

In a third embodiment of the present invention, source 16 of positive fluid pressure is a ventilator that is capable of generating positive pressure within the patient's airway during expiration, such as a BiPAP Synchrony Ventilator (Respironics Inc. Pittsburgh, Pa.). In this embodiment, prior to initiating the working cycle as described above, the user sets ventilation parameters for the BiPAP ventilator so as to achieve maximal insufflation with each delivered ventilator breath (by choosing an appropriate value for the inspiratory positive airway pressure—"IPAP") and so as to achieve a desired expiratory positive airway pressure between inexsufflation cycles, i.e. during the ventilator's expiratory cycle. Thereafter, the working cycle of inexsufflator 10 is generally as described previously. During the pause period between the termination of exsufflation and the initiation of the next insufflation by the ventilator, intrapulmonary pressure may be maintained at a supra-atmospheric PEEP level by the ventilator.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An inexsufflator for cough simulation to remove broncho-pulmonary secretions of a patient comprising:

a patient interface unit configured to permit fluid flow therethrough at a flow rate of at least 160 liters/minute;

a source of negative fluid pressure configured to generate the flow rate of at least 160 liters/minute; and a valve in communication with the patient interface unit, a port of the source of negative fluid pressure, and a port of a ventilator, said valve configured to selectively connect said patient interface unit with one of said port of said ventilator and said port of said source of negative fluid pressure and to selectively seal fluid flow between said patient interface unit and one of said port of the ventilator and said port of said source of negative fluid pressure, wherein actuation of the valve from a first position to a second position at or near lung capacity of the patient initiates exsufflation of the lung to simulate a cough.

2. The inexsufflator according to claim 1, wherein said ventilator comprises one of the following: a volume-cycled ventilator, a time-cycled ventilator, a pressure limited ventilator, or a bilevel positive airway pressure (BiPAP) ventilator.

3. The inexsufflator according to claim 1, wherein said patient interface unit comprises one of the following: a facemask, a tracheostomy tube, or an endotracheal ventilation tube.

4. The inexsufflator according to claim 1, wherein said valve comprises a manually actuated valve.

5. The inexsufflator according to claim 1 further comprising, a pressure sensor configured to sense one of a negative fluid pressure or a positive fluid pressure.

6. The inexsufflator according to claim 1, wherein said source of negative fluid pressure comprises a medical suction unit.

* * * * *